(12) United States Patent
Franke et al.

(10) Patent No.: US 11,964,140 B2
(45) Date of Patent: Apr. 23, 2024

(54) INJECTOR DEVICE

(71) Applicant: Sanofi, Paris (FR)

(72) Inventors: Beate Franke, Frankfurt am Main (DE); Ulrich Brueggemann, Bridgewater, NJ (US); Jeff Kablik, Bridgewater, NJ (US)

(73) Assignee: Sanofi, Paris (FR)

( * ) Notice: Subject to any disclaimer, the term of this patent is extended or adjusted under 35 U.S.C. 154(b) by 101 days.

(21) Appl. No.: 16/768,349

(22) PCT Filed: Dec. 3, 2018

(86) PCT No.: PCT/EP2018/083281
§ 371 (c)(1),
(2) Date: May 29, 2020

(87) PCT Pub. No.: WO2019/106202
PCT Pub. Date: Jun. 6, 2019

(65) Prior Publication Data
US 2020/0360621 A1 Nov. 19, 2020

(30) Foreign Application Priority Data
Dec. 1, 2017 (EP) ..................... 17306677

(51) Int. Cl.
*A61M 5/32* (2006.01)
*A61M 5/20* (2006.01)
*A61M 5/24* (2006.01)
(52) U.S. Cl.
CPC .......... *A61M 5/326* (2013.01); *A61M 5/3271* (2013.01); *A61M 2005/2013* (2013.01);
(Continued)

(58) Field of Classification Search
CPC ................ A61M 5/326; A61M 5/3271; A61M 2005/2073; A61M 2005/2474;
(Continued)

(56) References Cited

U.S. PATENT DOCUMENTS

2008/0177237 A1* 7/2008 Stonehouse ........... A61M 5/326
604/263
2015/0374927 A1 12/2015 Dasbach

FOREIGN PATENT DOCUMENTS

CN 103228306 7/2013
EP 3106190 12/2016
(Continued)

OTHER PUBLICATIONS

PCT International Preliminary Report on Patentability in International Appln. No. PCT/EP2018/083281, dated Jun. 2, 2020, 7 pages.
(Continued)

*Primary Examiner* — Robert J Utama
*Assistant Examiner* — Neeraja Gollamudi
(74) *Attorney, Agent, or Firm* — Fish & Richardson P.C.

(57) ABSTRACT

The present disclosure relates to an injector device having a housing, a cartridge with a reservoir for medicament, a needle unit with a needle, and a needle sleeve rotatably mounted to the housing about an axis. Prior to use of the injector device the needle is sealed from the reservoir, and at least one of the needle unit and the cartridge is axially slidably mounted to the housing. The needle sleeve includes an engagement member arranged to engage the needle unit and/or the cartridge. The engagement member is adapted such that rotation of the needle sleeve moves the needle unit and/or the cartridge in an axial direction to move the needle into fluid communication with the reservoir.

18 Claims, 9 Drawing Sheets

(52) U.S. Cl.
CPC ..... *A61M 5/2033* (2013.01); *A61M 2005/208* (2013.01); *A61M 5/2466* (2013.01)

(58) Field of Classification Search
CPC .... A61M 2005/3267; A61M 2005/247; A61M 5/3257; A61M 5/2466; A61M 5/3243; A61M 5/3245; A61M 5/20
See application file for complete search history.

(56) References Cited

FOREIGN PATENT DOCUMENTS

| | | | | |
|---|---|---|---|---|
| EP | 3106190 A1 | * | 12/2016 | .......... A61M 5/2455 |
| WO | WO 2012/072563 | | 6/2012 | |
| WO | WO 2015/062845 | | 5/2015 | |
| WO | WO 2016/202829 | | 12/2016 | |
| WO | WO 2017/029515 | | 2/2017 | |
| WO | WO 2017/089277 | | 6/2017 | |
| WO | WO 2017/089285 | | 6/2017 | |
| WO | WO-2017089284 A1 | * | 6/2017 | .......... A61M 5/2466 |
| WO | WO-2017089285 A1 | * | 6/2017 | ............. A61M 5/24 |
| WO | WO 2018/001790 | | 1/2018 | |
| WO | WO-2018001790 A1 | * | 1/2018 | ............. A61M 5/00 |

OTHER PUBLICATIONS

PCT International Search Report and Written Opinion in International Appln. No. PCT/EP2018/083281, dated Mar. 15, 2019, 9 pages.

\* cited by examiner

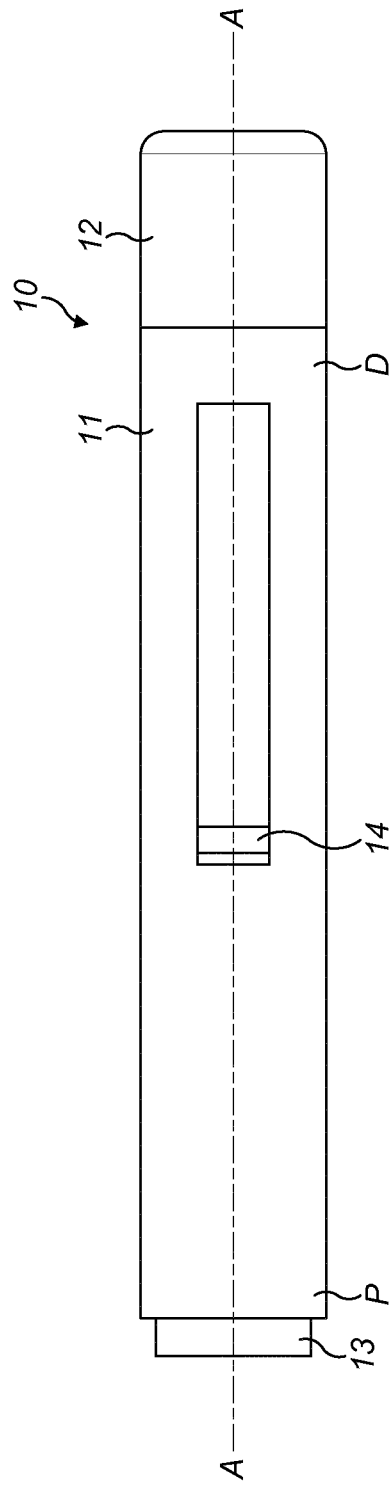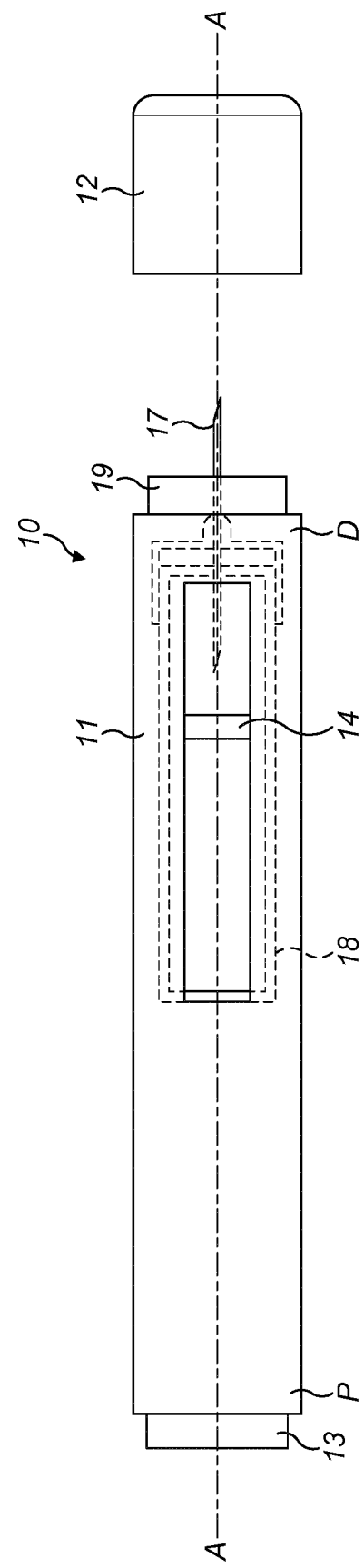

INJECTOR DEVICE

CROSS REFERENCE TO RELATED APPLICATIONS

The present application is the national stage entry of International Patent Application No. PCT/EP2018/083281, filed on Dec. 3, 2018, and claims priority to Application No. EP 17306677.0, filed on Dec. 1, 2017, the disclosures of which are incorporated herein by reference.

TECHNICAL FIELD

The present disclosure relates to an injector device for a medicament.

BACKGROUND

Cartridge injection devices, for example cartridge autoinjectors, typically have a sealed cartridge that contains a medicament and a needle that is initially separated from the cartridge. Before use of the injector device the cartridge and needle are combined so that the needle pierces the cartridge. A plunger can then be moved into the cartridge to dispense medicament through the needle for injection to a user.

SUMMARY

In certain aspects, an injector device having a cartridge with a reservoir for medicament that is initially sealed from a needle, and a mechanism for moving the needle into fluid communication with the reservoir prior to use is provided.

According to one aspect, there is provided an injector device comprising:
 a housing,
 a cartridge having a reservoir for medicament,
 a needle unit comprising a needle, wherein prior to the use of the injector device the needle is sealed from the reservoir, and
 a needle sleeve rotatably mounted to the housing about an axis,
 wherein at least one of the needle unit and the cartridge is axially slidably mounted to the housing, and
 wherein the needle sleeve comprises an engagement member arranged to engage the needle unit and/or the cartridge, the engagement member being adapted such that rotation of the needle sleeve moves the needle unit and/or the cartridge in an axial direction to move the needle into fluid communication with the reservoir.

In examples, the needle unit is slidably mounted to the housing, and the engaging member of needle sleeve moves the needle unit in an axial direction to move the needle into fluid communication with the reservoir.

In other examples, the cartridge is slidably mounted to the housing, and the engaging member of needle sleeve moves the cartridge in an axial direction to move the needle into fluid communication with the reservoir.

In some examples, the needle sleeve is axially slidably mounted to the housing, and after rotation of the needle sleeve the engagement member disengages from the needle unit and/or the cartridge so that needle sleeve can move axially independently of needle sleeve and cartridge.

The injector device may further comprise a slot arranged to prevent axial movement of the needle sleeve until after the needle sleeve has been rotated relative to the housing.

One of the housing and the needle sleeve may comprise the slot, and the other of the housing and the needle sleeve may comprise a protrusion adapted to engage the slot, and wherein the slot comprises a circumferential portion for rotation of the needle sleeve, and an axial portion for axial movement of the needle sleeve.

For example, the housing may comprise the slot, and the needle sleeve may comprise the protrusion adapted to engage the slot. In this case, the slot may comprise a circumferential portion for rotation of the needle sleeve, and an axial portion for axial movement of the needle sleeve.

In another example, the needle sleeve may comprise the slot, and the housing may comprise the protrusion adapted to engage the slot. In this case, the slot may comprise a circumferential portion for rotation of the needle sleeve, and an axial portion for axial movement of the needle sleeve.

The needle unit may comprise a needle body, and the needle body may be arranged to engage the cartridge and/or the housing during axial movement of the needle unit and/or cartridge.

For example, the needle body may engage an end of the cartridge. Alternatively, the needle body may engage a cartridge mounting portion of the housing which is proximal to the cartridge.

In some examples, the housing includes a tubular cartridge mounting portion that surrounds an end of the cartridge, and the needle body may be arranged to engage the tubular cartridge mounting portion.

The injector device may further comprise a guide arranged to guide the needle unit and/or the cartridge into engagement as the needle unit and/or cartridge move axially. The guide may additionally prevent rotation of the needle unit relative to the cartridge.

In some examples, the needle unit is axially slidably mounted in the housing and the cartridge is fixedly mounted to the housing. In these examples, the needle body may comprise a guide slot arranged to cooperate with a guide rail, and the guide rail may extend from the cartridge or from the housing.

In some examples the needle unit further comprises locking members arranged to lock the needle unit onto the cartridge or the housing after axial movement of the needle unit and/or cartridge has moved the needle into fluid communication with the reservoir.

In some examples, the needle unit is axially slidably mounted to the housing. In these examples, the needle unit may comprise a protrusion and the needle sleeve may comprise a helical member arranged to engage the protrusion and move the needle unit axially on rotation of the needle sleeve.

In other examples, the cartridge is axially slidably mounted to the housing. In these examples, the cartridge may comprise a protrusion and the needle sleeve may comprise a helical member arranged to engage the protrusion and move the cartridge axially on rotation of the needle sleeve.

In these examples, the helical member may be arranged such that rotation of the needle sleeve moves the helical member out of engagement with the protrusion. In this way, the needle sleeve is able to move in an axial direction independently of the needle unit and the cartridge.

The injector device of any of claims 1 to 9, further comprising a thread disposed between the needle unit and one of the cartridge or the housing, and wherein rotation of the needle sleeve is adapted to cause rotation of the needle unit or the cartridge such that the thread moves the needle unit or cartridge in an axial direction as the needle sleeve is rotated.

The cartridge may comprise a medicament in the reservoir.

In some embodiments, the needle sleeve is moveable relative to the housing from an extended position, wherein the needle sleeve covers an end of the needle, to a retracted position, wherein the end of the needle is exposed.

In some embodiments, when the needle sleeve is in the extended position, a distal end of the needle is located within the needle sleeve. In some embodiments, when the needle sleeve is in the retracted position, the end of the needle extends axially past a distal end of the needle sleeve. In some embodiments, when the needle sleeve is in the retracted position, a distal end of the needle is located outside of the needle sleeve.

In some embodiments, the injector device comprises a biasing member that biases the needle sleeve into the extended positon. The biasing member may be a spring.

In some embodiments, the needle sleeve is generally tubular. The needle sleeve may be generally cylindrical.

In some embodiments, the injector device comprises a cap. The cap may be removably attached to the housing.

According to another aspect of the present invention, there is also provided a method of using an injector device that comprises:
- a cartridge having a reservoir for medicament,
- a needle unit comprising a needle, wherein prior to the use of the injector device the needle is sealed from the reservoir, and
- a needle sleeve rotatably mounted to the housing about an axis, wherein the method comprises:
- rotating the needle sleeve about the axis to move the needle unit and/or the cartridge in an axial direction such that the needle is moved into fluid communication with the reservoir.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which:

FIG. 1A is a schematic side view of an injector device, and a removable cap;

FIG. 1B is a schematic side view of the injector device of FIG. 1A, with the cap removed from the housing;

DETAILED DESCRIPTION

Figure 2:
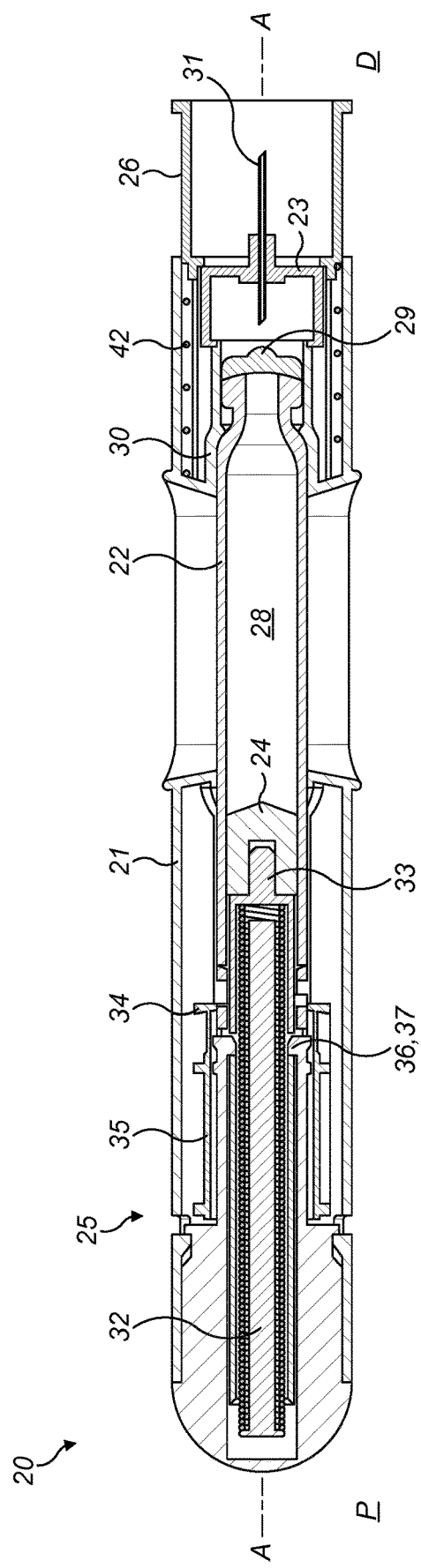
FIG. 2 is a cross-sectional view of an injector device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD), Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources, Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11, Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

FIG. 2 illustrates an example injector device 20 having a housing 21, a cartridge 22, a needle unit 23, and a needle sleeve 26. The injector device 20 further includes a piston 24 and a piston drive mechanism 25.

The cartridge 22 defines a reservoir 28 that contains a medicament and is mounted within the housing 21. A distal end D of the cartridge 22 is sealed by an end cap 29. A cartridge mounting portion 30 of the housing 21 supports the cartridge 22. As illustrated, a part of the cartridge mounting portion 30 is tubular and surrounds the distal end of the cartridge 22. This tubular part of the cartridge mounting portion 30 has an external surface disposed within the housing 21.

As shown in FIG. 2, in an initial condition the needle 31 of the needle unit 23 is spaced from the end cap 29 at the distal end of the cartridge 22. Before or during use of the injector device 20 the needle unit 23 is moved into engagement with the distal end of the cartridge 22 such that the needle 31 pierces the end cap 29 of the cartridge 22. In this way, medicament can be expelled from the reservoir 28 via the needle 31, as explained further hereinafter.

In the initial condition, illustrated in FIG. 2, the piston 24 is disposed at a proximal end of the reservoir 28 in the cartridge 22, and the piston drive mechanism 25 is disposed in the proximal end of the housing 21. The piston drive mechanism 25 comprises a spring 32, a plunger 33, and a catch 34. The spring 32 is arranged to urge the plunger 33 against the piston 24 and into the cartridge 22 to expel medicament from the reservoir 28 during use. In the initial condition before use, as illustrated, the spring 32 is held in a compressed state by a catch 34. Specifically, the catch 34 holds the plunger 33, which holds the spring 32 in a compressed state such that no force is applied to the piston 24. In this state, the piston drive mechanism 25 is preloaded.

As explained further hereinafter, the injector device 20 is actuated by an actuator, in this example the needle sleeve 26 that is rotationally and slidably movable within the housing 21 and protrudes from the distal end of the housing 21. In this way, during use, the needle sleeve 26 is placed against the user's skin and the injector device 20 is pushed towards the user's skin while holding the housing 21, this moves the needle sleeve 26 in a proximal direction, into the housing 21.

The needle sleeve 26 acts to release the catch 34 once the needle sleeve 26 has moved into the housing 21 in a proximal direction. Once the catch 34 is released, the spring 32 urges the plunger 33 against the piston 24 and into the reservoir 28.

As illustrated in FIG. 2, the catch 34 may include a tubular element 35 that surrounds the plunger 33 and spring 32. The tubular element 35 includes protrusions 36 that engage recesses 37 in the plunger 33, such that in the position illustrated in FIG. 2 the plunger 33 is prevented from moving in a distal direction by the protrusions 36 and the recesses 37.

As the needle sleeve 26 is moved proximally into the housing 21, an end of the needle sleeve 26 engages the tubular element 35, causing the tubular element 35 to rotate about the axis A of the injector device 20. This rotation causes the protrusions 36 to disengage from the recesses 37, thereby releasing the plunger 33, which then moves under the force of the spring 32 into the reservoir 28.

In one example, the end of the needle sleeve 26 that engages the tubular element 35 may comprise a chamfer (i.e. angled edge) that engages a protrusion on the tubular element 35 to cause the rotation. In other examples, the tubular element 35 may comprise a chamfer (i.e. angled edge) that is engaged by a protrusion on the needle sleeve 26 to cause the rotation.

In other examples, the catch 34 may comprise arms that include the protrusions that engage the plunger 33. In this case, the needle sleeve 26 might deflect the arms by lifting them to disengage the protrusions from the recesses, thereby releasing the plunger 33.

A biasing member, for example a spring 42, may be arranged to act between the housing 21 and the needle sleeve 26 to urge the needle sleeve 26 in a distal direction so that it protrudes from the distal end of the housing 21.

Before or during use, the needle unit 23 is combined with the cartridge 22 before the catch 34 is released. As explained below, rotating the needle sleeve 26 about the axis A causes one of the needle unit 23 or the cartridge 22 to move axially within the housing 21 so that the needle 31 is placed in fluid communication with the reservoir 28. A subsequent movement of the needle sleeve 26 in a proximal direction releases the catch 34 so that plunger 33 begins delivery of the medicament via the needle 31.

Figure 3:
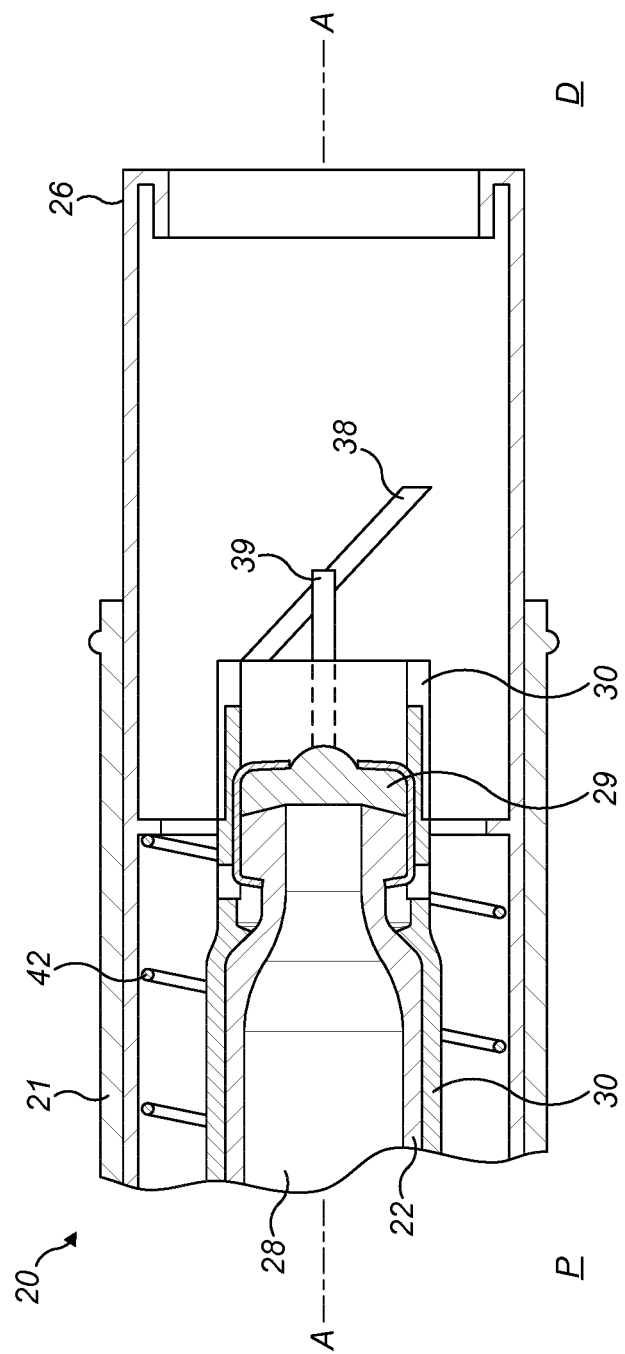
FIG. 3 is cross-sectional view of the needle-end of the injector device.

FIG. 3 illustrates the distal end of the injector device 20, without the needle unit 23. As shown, the needle sleeve 26 protrudes from a distal end of the housing 21. The needle sleeve 26 is slidably mounted to the housing 21, so that the needle sleeve 26 can move into the housing 21 in a proximal direction. A spring 42 is arranged to urge the needle sleeve 26 in a distal direction, i.e. to an extended position. The cartridge 22 is mounted within the housing 21, and in particular a tubular cartridge mounting portion 30 of the housing 21 surrounds the distal end of the cartridge 22.

As illustrated, the needle sleeve 26 includes a helical guide 38 arranged on an internal surface of the needle sleeve 26, extending partially about the internal circumference of the needle sleeve 26. In examples, the needle sleeve 26 may comprise one or more helical guides 38, for example two helical guides 38, or three helical guides 38.

As shown in FIG. 3, the cartridge mounting portion 30 of the housing 21 includes a linear guide in the form of a rail 39 that extends axially along the cartridge mounting portion 30. As illustrated, the rail 39 may extend past the distal end of the cartridge mounting portion 30. The rail 39 is located on an outer surface of the cartridge mounting portion 30, within the housing 21.

Figure 4A:
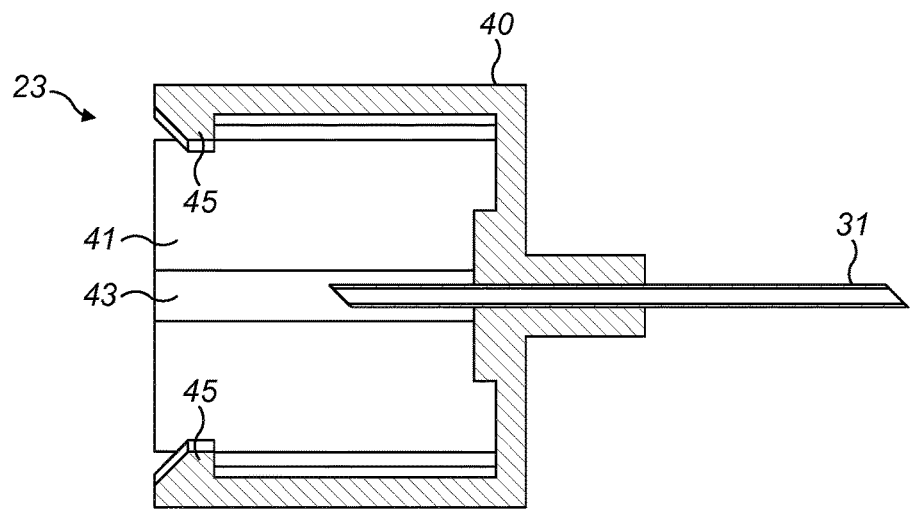
FIGS. 4A to 4C show the needle unit of the injector device.
Figure 4B:
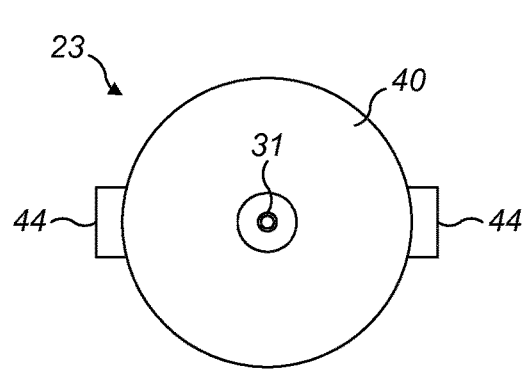
Figure 4C:
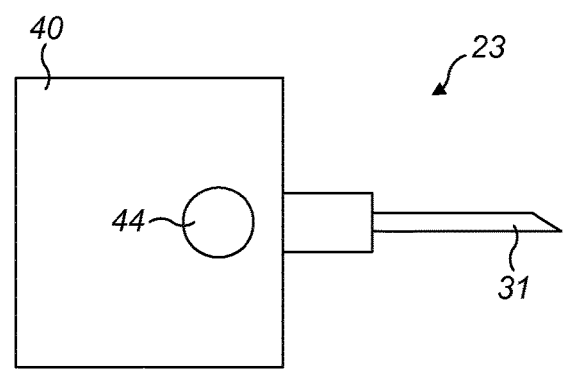

FIGS. 4A to 4C illustrate a needle unit 23 that may be used with the housing 21, needle sleeve 26, and cartridge 22 of FIG. 3. As shown in FIG. 4A, the needle unit 23 includes a needle body 40 to which a needle 31 is mounted. The needle body 40 includes a recess 41. The recess 41 is adapted to be positioned over the cartridge mounting portion 30 of the housing 21 (see FIG. 3) when the needle unit 23 is combined with the cartridge 22 (see FIG. 3) during use of the injector device 20.

As shown in FIG. 4A, and referring to FIG. 3, the needle body 40 includes a groove 43 arranged to cooperate with the rail 39 on the cartridge mounting portion 30 of the housing 21. The groove 43 is located on the internal surface of the needle body 40, in the recess 41. The cooperation of the rail 39 and the groove 43 prevents rotation of the needle unit 23 relative to the housing 21 and cartridge 22, and guides the needle unit 23 in an axial direction when the helical guide 38 of the needle sleeve 26 pushes the needle unit 23 onto the cartridge 22, as explained hereinafter.

As shown in FIGS. 4B and 4C, the outer surface of the needle body 40 includes protrusions 44. In this example, the external surface of the needle body 40 includes two protrusions 44, but it will be appreciated that one protrusion 44 is provided for each helical guide 38. The protrusions are generally circular, but may be other shapes. The protrusions 44 are equally spaced about the circumference of the needle body 40.

Referring to FIGS. 3, and 4A to 4C, the protrusions 44 on the needle body 40 are arranged to engage with the helical guides 38 on the needle sleeve 26 such that rotation of the needle sleeve 26 causes axial movement of the needle unit 23 towards the cartridge 22. In this way, during use of the injector device 20, the user rotates the needle sleeve 26 to engage the needle unit 23 with the cartridge 22 and place the needle 31 in fluid communication with the reservoir 28 before the injection process is started.

Figure 5A:
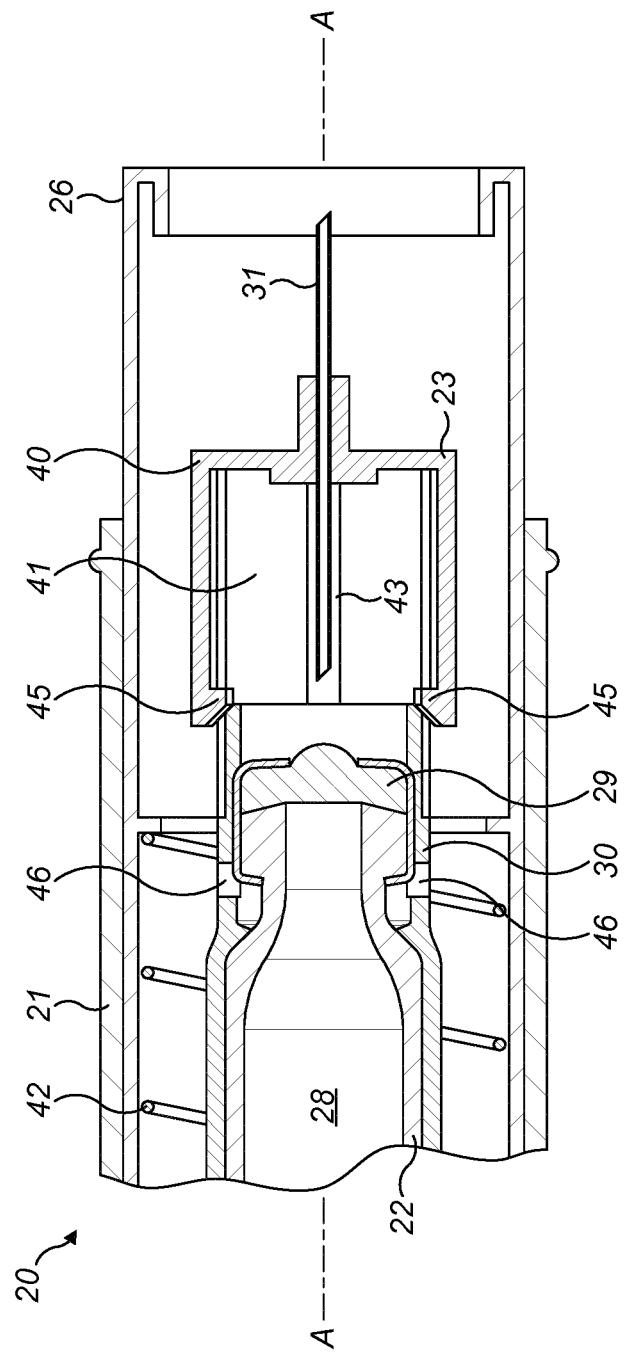
FIGS. 5A to 5C illustrate operation of the injector device.
Figure 5B:
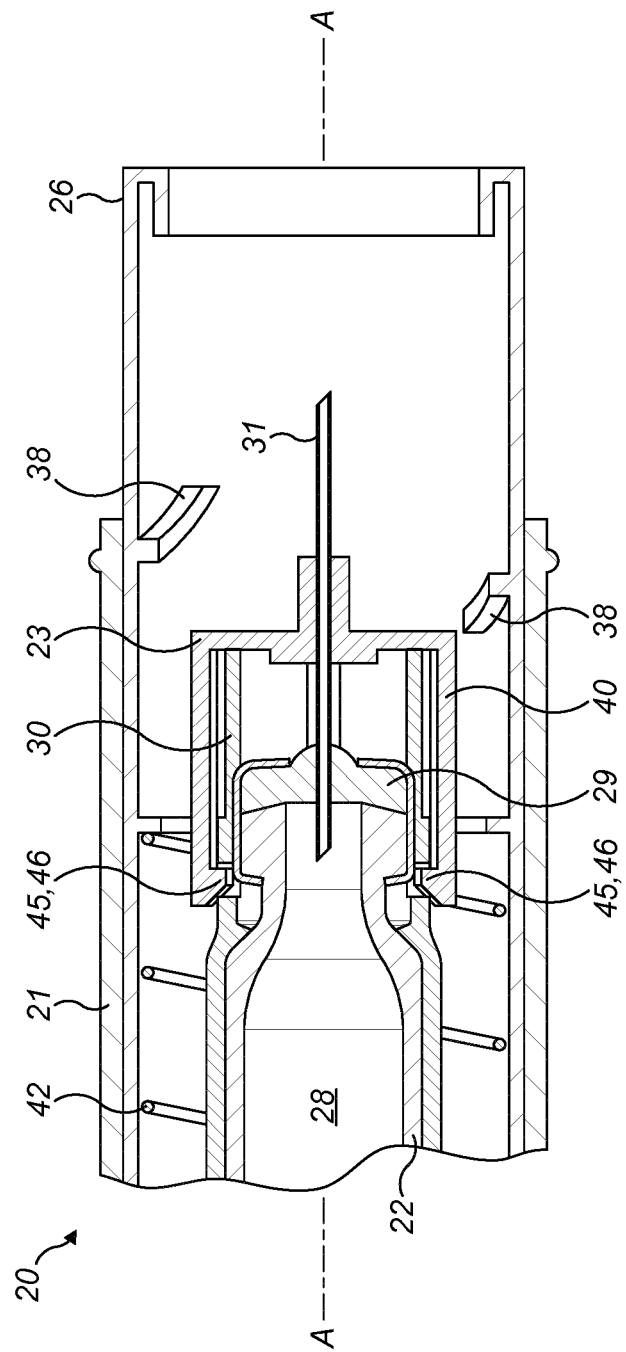
Figure 5C:
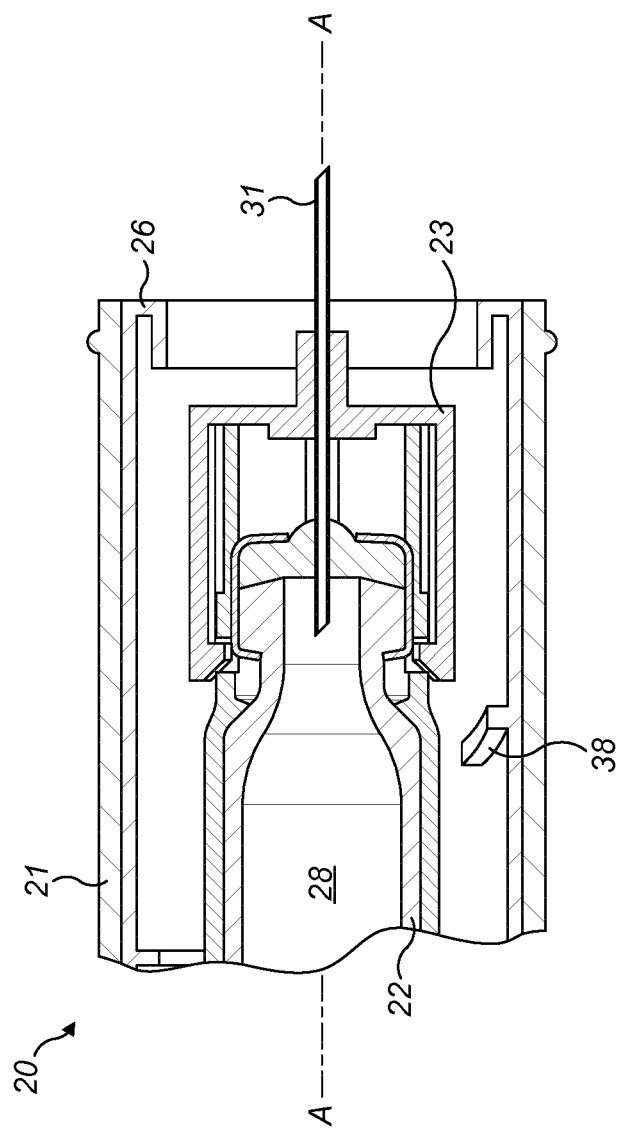

FIGS. 5A to 5C illustrate the process of combining of the needle unit 23 and cartridge 22.

As shown in FIG. 5A, and referring also to FIGS. 3 and 4A to 4C, in this initial position the needle unit 23 is spaced from the cartridge 22. The needle sleeve 26 is in an extended position and covers the needle 31. In this position, the needle unit 23 is held in place by a combination of the engagement between the protrusions 44 and helical guides 38, the engagement between a proximal end of the needle body 40 and the cartridge mounting portion 30 of the housing 21, and engagement between the rail 39 and groove 43.

As the needle sleeve 26 is rotated the engagement between the helical guides 38 on the needle sleeve 26 and the protrusions 44 on the needle unit 23 drive the needle unit 23 in an axial direction towards the cartridge 22. The rail 39 and groove 43 prevent rotation of the needle unit 23 and guide the needle unit 23 onto the cartridge mounting portion 30.

As shown in FIG. 5A, the proximal end of the needle body 40 includes catches 45 that initially have to be deflected to allow the needle body 40 to move over the cartridge mounting portion 30 of the housing 21. In the initial position, shown in FIG. 5A, engagement between the catches 45 and the cartridge mounting portion 30 help to hold the needle unit 23 in position within the injector device 20.

FIG. 5B shows the injector device 20 after the needle sleeve 26 has been rotated to move the needle unit 23 into engagement with the cartridge 22. As shown, the catches 45 on the proximal end of the needle body 40 have engaged with recesses 46 on the cartridge mounting portion 30, so that the needle unit 23 is secured in place on the cartridge mounting portion 30. Also, a proximal end of the needle 31 has pierced the end cap 29 of the cartridge 22, so that the needle 31 is in fluid communication with the reservoir 28. The needle sleeve 26 remains in an extended position due to the action of the spring 42.

Due to the rotation of the needle sleeve 26 the helical guides 38 have disengaged from the protrusions (44, see FIGS. 4A to 4C), so that the needle sleeve 26 is able to move axially independently of the needle unit 23.

FIG. 5C shows the injector device 20 after the injector device 20 has been pressed against the user's skin to start the injection process. As illustrated, the needle sleeve 26 has moved proximally into the housing 21, exposing the needle 31 so that the needle 31 can pierce the user's skin. Also, as explained previously, proximal movement of the needle sleeve 26 into the housing 21 releases the catch (34, see FIG. 2) of the piston drive mechanism (25, see FIG. 2) to release the plunger (33, see FIG. 2), and the spring (32, see FIG. 2) then drives the piston (24, see FIG. 2) into the cartridge 22 to dispense medicament from the reservoir 28 via the needle 31.

After use, the spring 42 urges the needle sleeve 26 back to an extended position to re-cover the needle 31.

Figure 6:
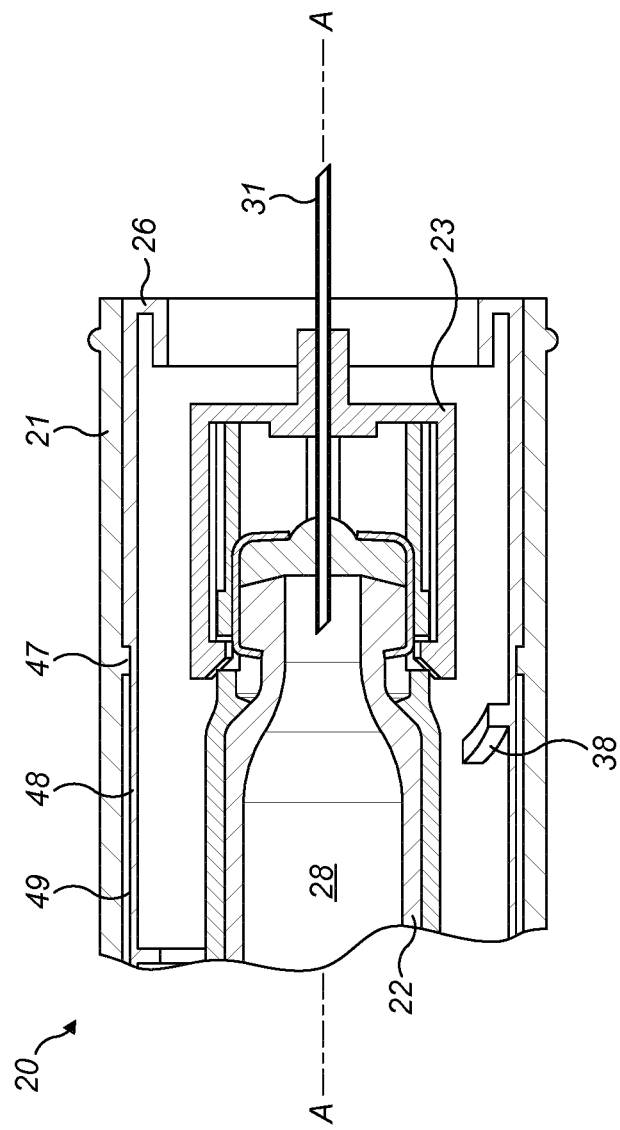
FIG. 6 shows the needle-end of an alternative injector device.

As illustrated in FIG. 6, to prevent the needle sleeve 26 from being moved proximally into the housing 21 before it has been rotated to engage the needle unit 23 and cartridge 22, the housing may include a protrusion 47 that engages a slot 48 on the needle sleeve 26, and the slot 48 and protrusion 47 may be arranged to only permit axial movement of the needle sleeve 26 after the needle sleeve 26 has been rotated.

In this example, the slot 48 is 'L' shaped, having a circumferentially extending portion (not illustrated) and an axially extending portion 49. In the initial position, the protrusion 47 on the housing 21 is located in the circumferentially extending portion of the slot 48, so that only rotation of the needle sleeve 26 is permitted. Once the needle sleeve 26 has been rotated the protrusion 47 is disposed in the axially extending portion 49 of the slot 48, so that the needle sleeve 26 can move axially towards the housing 21 to expose the needle 31 and trigger the piston drive mechanism (25, see FIG. 2).

It will be appreciated that in other examples the needle sleeve 26 may comprise the protrusion 47 and the housing 21 may comprise the slot 48.

Figure 7A:
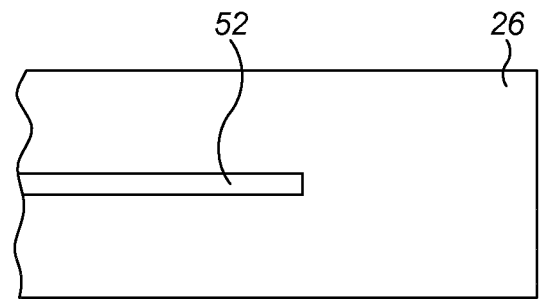
FIG. 7A shows the needle sleeve of an alternative injector device.
Figure 7B:
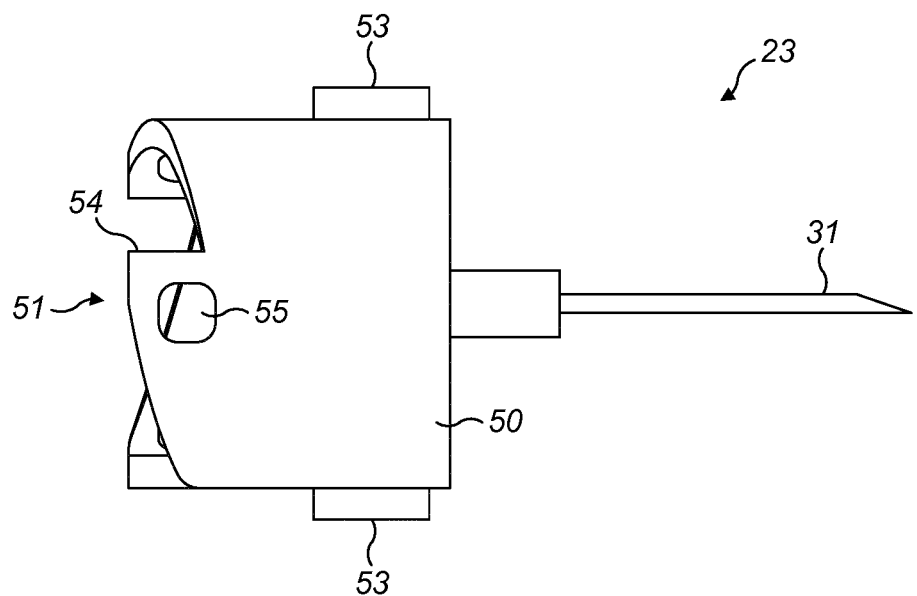
FIG. 7B shows the needle unit of the injector device of FIG. 7A.

FIGS. 7A and 7B illustrate an alternative example injector device 20. In particular FIG. 7A illustrates the distal end of the needle sleeve 26 and FIG. 7B illustrates the needle unit 23. The needle sleeve 26 of FIG. 7A and needle unit 23 of FIG. 7B can be used with the injector device 20 of FIG. 3, but in this example, the needle unit 23 is rotatably mounted within the housing 21 and there is no rail and groove (39, 43) as described with reference to previous examples.

Referring to FIGS. 7A, 7B and 3, the needle unit 23 has a needle body 50 having a recess 51, and an internal thread in the recess 51. The internal thread is arranged to engage with an external thread on the cartridge mounting portion 30 of the housing 21, or with an external thread on the cartridge 22. In an initial position the thread is aligned or partially started, such that on rotation of the needle unit 23 (explained below) the thread moves the needle unit 23 axially into engaged with the cartridge 22. In this way, the thread acts to guide the needle unit 23 into engagement with the cartridge 22 when the needle sleeve 26 is rotated.

The internal surface of the needle sleeve 26 includes a groove 52, preferably two grooves 52. The external surface of the needle body 50 includes a protrusion 53, preferably two protrusions 53, that engage with the grooves 52 of the needle sleeve 26. In this way, rotating the needle sleeve 26 in the housing 21 causes rotation of the needle unit 23 within the housing 21, and the thread moves the needle unit 23 axially into engagement with the cartridge 22 so that the needle 31 is placed in fluid communication with the reservoir 28.

As shown in FIG. 7B, the needle unit 23 may also include end stops 54 that engage a part of the cartridge mounting portion 30 after the needle unit 23 has been rotated onto the cartridge mounting portion 30 by the thread. Additionally or alternatively, recesses 55 may be provided to engage with catches on the cartridge mounting portion 30, to secure the needle unit 23 on the cartridge mounting portion 30.

The threaded connection between the needle unit 23 and cartridge mounting portion 30 may have a high pitch, so that comparatively less rotation is needed to achieve the desired axial movement. For example, the rotation may be between 30 and 120 degrees, or about 90 degrees. However, the rotation may be greater than 120 degrees, for example 180 degrees.

In various examples, the threaded connection may comprise an external thread on the cartridge mounting portion 30 and an internal thread on the needle unit 23, or alternatively one of the internal and external threads may be replaced by a protrusion arranged to engage the other thread, so that on rotation of the needle sleeve 23 the protrusion follows the path of the thread and moves the needle unit 23 into engagement with the cartridge 22.

In this example, similarly to as explained with reference to FIG. 6, an shaped slot and protrusion may be arranged between the housing 21 and the needle sleeve 26 to prevent axial movement of the needle sleeve 26 prior to rotation of the needle sleeve 26 to engage the needle unit 23 and cartridge 22.

In other examples similar to those described above, the needle unit 23 is fixedly mounted to the housing 21 and the cartridge 22 is axially slidably mounted to the housing 21. In these examples, rotation of the needle sleeve 26 causes the cartridge 22 to be moved axially into engagement with the needle unit 23.

For example, similarly to the example of FIGS. 3 to 50, the needle unit 23 may be fixedly mounted to the housing 21, the cartridge 22 may be movable in an axial direction, and the helical guides 38 of the needle sleeve 36 may be arranged to engage protrusions on the cartridge 22 such that rotation of the needle sleeve 26 moves the cartridge 22 in an axial distal direction to engage the needle unit 23. Similarly to the example of FIGS. 7A and 7B, rotation of the needle sleeve 26 may cause rotation of the cartridge 22 so that the threaded connection between the cartridge 22 and needle unit 23 moves the cartridge 22 in an axial distal direction into engagement with the needle unit 23.

Furthermore, in the examples described herein a cartridge mounting portion 30 of the housing 21 surrounds the distal end of the cartridge 22 and is engaged by the needle unit 23 during use. However, it will be appreciated that the features and function of the cartridge mounting portion 30 may be on the cartridge 22 itself. For example, the housing 21 may not surround the distal end of the cartridge 22, and the distal end of the cartridge 22 may include the features of the cartridge mounting portion 30 described previously, for example recesses 46, or a thread, or a rail 39.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.), In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in certain aspects of the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An injector device comprising:
a housing;
a cartridge having a reservoir for medicament;
a needle unit comprising a needle, wherein prior to use of the injector device the needle is sealed from the reservoir; and
a needle sleeve rotatably mounted to the housing about an axis, wherein a distal end of the needle sleeve defines an opening configured to allow a distal end of the needle to pass through,
wherein at least one of the needle unit or the cartridge is axially slidably mounted to the housing, and
wherein the needle sleeve comprises an engagement member arranged to engage the needle unit or the cartridge, the engagement member being adapted such that rotation of the needle sleeve moves the needle unit or the cartridge in an axial direction to move the needle into fluid communication with the reservoir, wherein the needle sleeve is axially slidably mounted to the housing, and wherein after the rotation of the needle sleeve, the engagement member disengages from the needle unit or the cartridge so that the needle sleeve can move axially independently of the needle unit and the cartridge.

2. The injector device of claim 1, further comprising a slot arranged to prevent axial movement of the needle sleeve until after the rotation of the needle sleeve.

3. The injector device of claim 2, wherein one of the housing or the needle sleeve comprises the slot, and the other of the housing or the needle sleeve comprises a protrusion adapted to engage the slot, and wherein the slot comprises a circumferential portion for allowing the rotation of the needle sleeve, and an axial portion for allowing the axial movement of the needle sleeve.

4. The injector device of claim 1, wherein the needle unit comprises a needle body, the needle body being arranged to engage the cartridge and/or the housing during axial movement of the needle unit or the cartridge.

5. The injector device of claim 4, wherein the needle unit is axially slidably mounted in the housing and the cartridge is fixedly mounted to the housing, and wherein the needle body comprises a groove arranged to cooperate with a guide rail, the guide rail extending from the cartridge or from the housing.

6. The injector device of claim 1, further comprising a guide arranged to guide the needle unit into engagement with the cartridge as the needle unit or the cartridge moves axially.

7. The injector device of claim 6, wherein the guide prevents rotation of the needle unit relative to the cartridge.

8. The injector device of claim 1, wherein the needle unit further comprises catches arranged to lock the needle unit onto the cartridge or the housing after axial movement of the needle unit or the cartridge moves the needle into with the reservoir.

9. The injector device of claim 1, wherein the needle unit is axially slidably mounted to the housing, and wherein the needle unit comprises a protrusion and the engagement member of the needle sleeve comprises a helical member arranged to engage the protrusion and move the needle unit axially in response to the rotation of the needle sleeve.

10. The injector device of claim 9, wherein the helical member is arranged such that the rotation of the needle sleeve moves the helical member out of engagement with the protrusion.

11. The injector device of claim 1, wherein the cartridge is axially slidably mounted to the housing, and wherein the cartridge comprises a protrusion and the engagement member of the needle sleeve comprises a helical member arranged to engage the protrusion and move the cartridge axially in response to the rotation of the needle sleeve.

12. The injector device of claim 1, further comprising a thread disposed between the needle unit and one of the cartridge or the housing, wherein the rotation of the needle sleeve is adapted to cause rotation of the needle unit or the cartridge such that the thread moves the needle unit or the cartridge in the axial direction as the needle sleeve is rotated.

13. The injector device of claim 1, wherein the cartridge comprises the medicament in the reservoir.

14. The injector device of claim 1, wherein the needle sleeve is movable relative to the housing from an extended position in which the needle sleeve covers an end of the needle to a retracted position in which the end of the needle is exposed.

15. A method of using an injector device, the method comprising:
rotating a needle sleeve of the injector device about an axis relative to a housing of the injector device to move a needle unit of the injector device or a cartridge of the injector device in an axial direction such that a needle of the needle unit is moved into fluid communication with a reservoir of the cartridge, wherein rotating the needle sleeve of the injector device comprises causing an engagement member of the needle sleeve to disengage from the needle unit or the cartridge of the injector device so that the needle sleeve can move axially independently of the needle unit and the cartridge; and
initiating an injection of a medicament from the injector device, comprising:
causing a distal end of the needle to pass through an opening defined in a distal end of the needle sleeve.

16. The method of claim 15, wherein initiating the injection of the medicament comprises moving the needle sleeve of the injector device in a proximal direction.

17. The method of claim 16, wherein rotating the needle sleeve of the injector device comprises causing a protrusion on one of the needle sleeve or the housing to move to a portion of a slot on the other of the needle sleeve or the housing such that the needle sleeve of the injector device can be moved in the proximal direction.

18. The method of claim 15, wherein rotating the needle sleeve of the injector device comprises causing the cartridge of the injector device to move axially.

* * * * *

UNITED STATES PATENT AND TRADEMARK OFFICE
CERTIFICATE OF CORRECTION

PATENT NO. : 11,964,140 B2
APPLICATION NO. : 16/768349
DATED : April 23, 2024
INVENTOR(S) : Beate Franke, Ulrich Brueggemann and Jeff Kablik It is certified that error appears in the above-identified patent and that said Letters Patent is hereby corrected as shown below:

In the Claims

Column 14, Line 66, Claim 8, before "with", insert -- fluid communication --

Signed and Sealed this
Eleventh Day of June, 2024

Katherine Kelly Vidal
*Director of the United States Patent and Trademark Office*